US009373486B2

(12) United States Patent
Lock

(10) Patent No.: US 9,373,486 B2
(45) Date of Patent: Jun. 21, 2016

(54) SPECIES DETECTION USING MASS SPECTROMETRY

(71) Applicant: DH TECHNOLOGIES DEVELOPMENT PTE. LTD., Singapore (SG)

(72) Inventor: Stephen Lock, West Yorkshire (GB)

(73) Assignee: DH Technologies Development Pte. Ltd. (SG)

( * ) Notice: Subject to any disclaimer, the term of this patent is extended or adjusted under 35 U.S.C. 154(b) by 0 days.

(21) Appl. No.: 14/889,137

(22) PCT Filed: May 19, 2014

(86) PCT No.: PCT/IB2014/000768
§ 371 (c)(1),
(2) Date: Nov. 4, 2015

(87) PCT Pub. No.: WO2014/188251
PCT Pub. Date: Nov. 27, 2014

(65) Prior Publication Data
US 2016/0086782 A1    Mar. 24, 2016

Related U.S. Application Data

(60) Provisional application No. 61/825,935, filed on May 21, 2013.

(51) Int. Cl.
*H01J 49/00* (2006.01)
*G01N 33/12* (2006.01)

(52) U.S. Cl.
CPC ............ *H01J 49/0036* (2013.01); *G01N 33/12* (2013.01); *H01J 49/004* (2013.01)

(58) Field of Classification Search
USPC ................................................. 250/281, 282
See application file for complete search history.

(56) References Cited

U.S. PATENT DOCUMENTS

| 2006/0094121 A1 | 5/2006 | Reid et al. | |
| 2008/0021687 A1* | 1/2008 | Hunter | H01J 49/004 703/11 |
| 2011/0250618 A1 | 10/2011 | Nelson et al. | |
| 2012/0164741 A1 | 6/2012 | Chen et al. | |

FOREIGN PATENT DOCUMENTS

| WO | 2010086386 A1 | 8/2010 |
| WO | 2010105112 A1 | 9/2010 |

OTHER PUBLICATIONS

International Search Report and Written Opinion for PCT/IB2014/000768, mailed Sep. 25, 2014.

* cited by examiner

*Primary Examiner* — Kiet T Nguyen
(74) *Attorney, Agent, or Firm* — John R. Kasha; Kelly L. Kasha; Kasha Law LLC

(57) ABSTRACT

Systems and methods are provided for species detection using mass spectrometry. In various embodiments, a multiple reaction monitoring (MRM) experiment is performed on a sample targeting one or more peptide transitions that are unique to one or more species using a tandem mass spectrometer. One or more measured product ion spectra are received from the tandem mass spectrometer using the processor. The one or more measured product ion spectra are compared to product ions of the one or more peptide transitions that are unique to one or more species using the processor. One or more species of the sample are detected by reporting product ions of the one or more peptide transitions that are unique to one or more species that match the one or more measured product ion spectra using the processor.

20 Claims, 13 Drawing Sheets

| MRM transition | DP (V) | CE (V) |
|---|---|---|
| 309/160 | 120 | 28 |
| 309/120 | 120 | 32 |
| 309/188 | 120 | 22 |

SPECIES DETECTION USING MASS SPECTROMETRY

CROSS REFERENCE TO RELATED APPLICATION

This application claims the benefit of U.S. Provisional Patent Application Ser. No. 61/825,935, filed May 21, 2013, the content of which is incorporated by reference herein in its entirety.

INTRODUCTION

The Food Standards Agency (FSA), an independent government department of the United Kingdom, announced in January of 2013 that deoxyribonucleic acid (DNA) molecules of horse and/or pig had been identified in beef products sold by several supermarket chains. Follow-up testing across Europe and beyond has revealed widespread incidences of such contamination.

However, most existing testing methods are based on detection of a species'-specific DNA in meat, using the polymerase chain reaction (PCR)—which is time consuming and does not detect or identify proteins. This is a concern because DNA can be easily disrupted or removed during standard meat processing and food manufacturing. As a result, horse tissue or other contaminants remain undetected in food samples, despite strong presence of the contaminating proteins. An alternative protein-based method, enzyme-linked immunosorbent assay (ELISA), can be used to complement the DNA testing. However, the ELISA method detects only one part of the protein and not multiple protein markers.

SUMMARY

A system is disclosed for species detection using tandem mass spectrometry. The system includes a tandem mass spectrometer and a processor. The tandem mass spectrometer performs a multiple reaction monitoring (MRM) experiment on a sample targeting one or more peptide transitions that are unique to one or more species. The processor receives one or more measured product ion spectra from the tandem mass spectrometer, and compares the one or more measured product ion spectra to product ions of the one or more peptide transitions that are unique to one or more species. The processor further detects one or more species of the sample by reporting product ions of the one or more peptide transitions that are unique to one or more species that match the one or more measured product ion spectra.

A method is disclosed for species detection using tandem mass spectrometry. An MRM experiment is performed on a sample targeting one or more peptide transitions that are unique to one or more species using a tandem mass spectrometer. One or more measured product ion spectra are received from the tandem mass spectrometer using the processor. The one or more measured product ion spectra are compared to product ions of the one or more peptide transitions that are unique to one or more species using the processor. One or more species of the sample are detected by reporting product ions of the one or more peptide transitions that are unique to one or more species that match the one or more measured product ion spectra using the processor.

A computer program product is disclosed that includes a non-transitory and tangible computer-readable storage medium whose contents include a program with instructions being executed on a processor so as to perform a method for species detection using mass spectrometry.

The method includes providing a system, wherein the system comprises one or more distinct software modules, and wherein the distinct software modules comprise a measurement module and a detection module. The measurement module receives one or more measured product ion spectra from the tandem mass spectrometer that performs an MRM experiment on a sample targeting one or more peptide transitions that are unique to one or more species.

The detection module compares the one or more measured product ion spectra to product ions of the one or more peptide transitions that are unique to one or more species. The detection module detects one or more species of the sample by reporting product ions of the one or more peptide transitions that are unique to one or more species that match the one or more measured product ion spectra.

BRIEF DESCRIPTION OF THE DRAWINGS

The skilled artisan will understand that the drawings, described below, are for illustration purposes only. The drawings are not intended to limit the scope of the present teachings in any way.

Before one or more embodiments of the invention are described in detail, one skilled in the art will appreciate that the invention is not limited in its application to the details of construction, the arrangements of components, and the arrangement of steps set forth in the following detailed. The invention is capable of other embodiments and of being practiced or being carried out in various ways. Also, it is to be understood that the phraseology and terminology used herein is for the purpose of description and should not be regarded as limiting.

DESCRIPTION OF VARIOUS EMBODIMENTS

Computer-Implemented System

Figure 1:
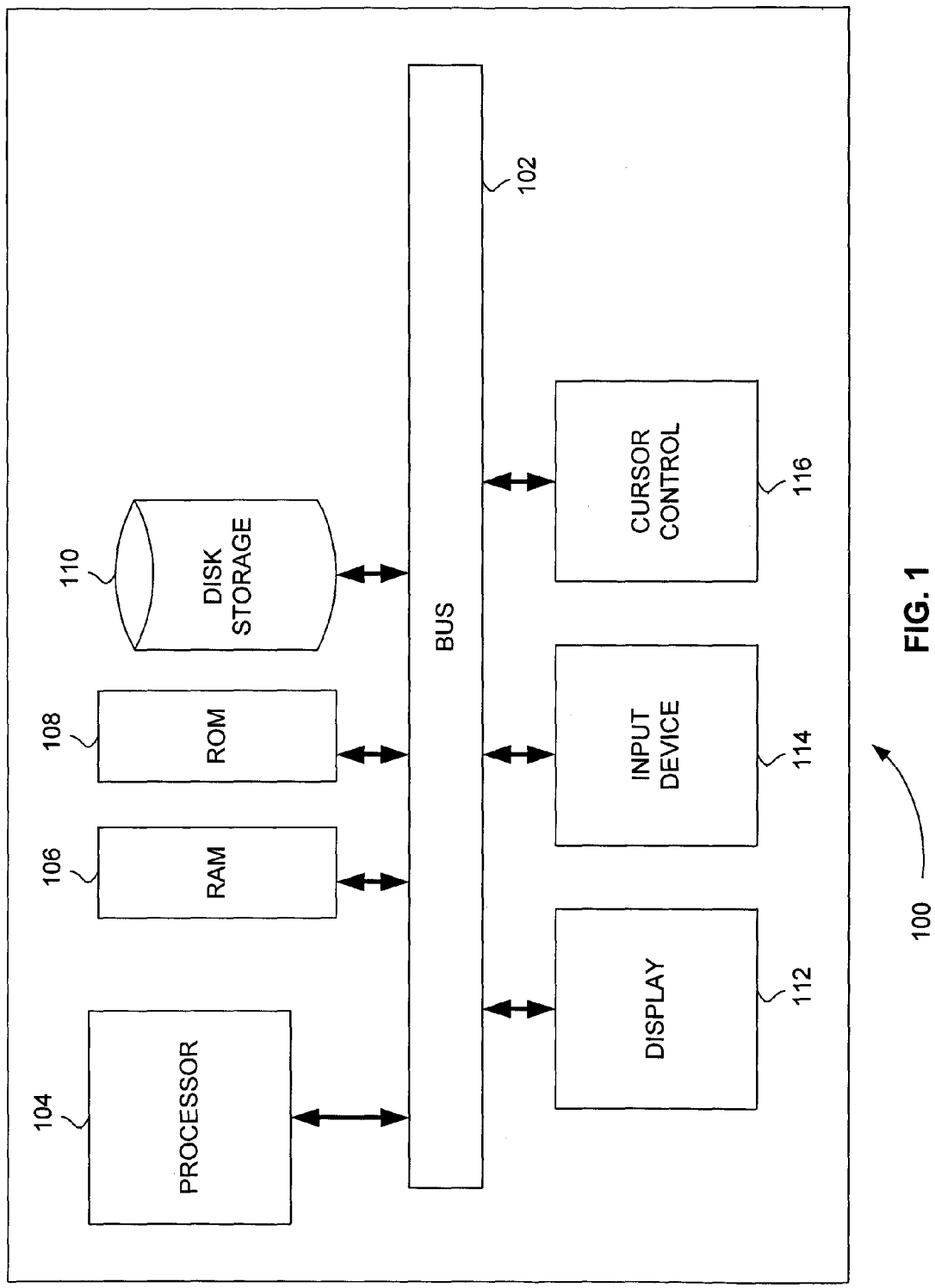
FIG. 1 is a block diagram that illustrates a computer system, upon which embodiments of the present teachings may be implemented.

FIG. 1 is a block diagram that illustrates a computer system 100, upon which embodiments of the present teachings may be implemented. Computer system 100 includes a bus 102 or other communication mechanism for communicating information, and a processor 104 coupled with bus 102 for processing information. Computer system 100 also includes a memory 106, which can be a random access memory (RAM) or other dynamic storage device, coupled to bus 102 for storing instructions to be executed by processor 104. Memory 106 also may be used for storing temporary variables or other intermediate information during execution of instructions to be executed by processor 104. Computer system 100 further includes a read only memory (ROM) 108 or other static storage device coupled to bus 102 for storing static information and instructions for processor 104. A storage device 110, such as a magnetic disk or optical disk, is provided and coupled to bus 102 for storing information and instructions.

Computer system 100 may be coupled via bus 102 to a display 112, such as a cathode ray tube (CRT) or liquid crystal display (LCD), for displaying information to a computer user. An input device 114, including alphanumeric and other keys, is coupled to bus 102 for communicating information and command selections to processor 104. Another type of user input device is cursor control 116, such as a mouse, a trackball or cursor direction keys for communicating direction information and command selections to processor 104 and for controlling cursor movement on display 112. This input device typically has two degrees of freedom in two axes, a first axis (i.e., x) and a second axis (i.e., y), that allows the device to specify positions in a plane.

A computer system 100 can perform the present teachings. Consistent with certain implementations of the present teachings, results are provided by computer system 100 in response to processor 104 executing one or more sequences of one or more instructions contained in memory 106. Such instructions may be read into memory 106 from another computer-readable medium, such as storage device 110. Execution of the sequences of instructions contained in memory 106 causes processor 104 to perform the process described herein. Alternatively hard-wired circuitry may be used in place of or in combination with software instructions to implement the present teachings. Thus implementations of the present teachings are not limited to any specific combination of hardware circuitry and software.

In various embodiments, computer system 100 can be connected to one or more other computer systems, like computer system 100, across a network to form a networked system. The network can include a private network or a public network such as the Internet. In the networked system, one or more computer systems can store and serve the data to other computer systems. The one or more computer systems that store and serve the data can be referred to as servers or the cloud, in a cloud computing scenario. The one or more computer systems can include one or more web servers, for example. The other computer systems that send and receive data to and from the servers or the cloud can be referred to as client or cloud devices, for example.

The term "computer-readable medium" as used herein refers to any media that participates in providing instructions to processor 104 for execution. Such a medium may take many forms, including but not limited to, non-volatile media, volatile media, and transmission media. Non-volatile media includes, for example, optical or magnetic disks, such as storage device 110. Volatile media includes dynamic memory, such as memory 106. Transmission media includes coaxial cables, copper wire, and fiber optics, including the wires that comprise bus 102.

Common forms of computer-readable media or computer program products include, for example, a floppy disk, a flexible disk, hard disk, magnetic tape, or any other magnetic medium, a CD-ROM, digital video disc (DVD), a Blu-ray Disc, any other optical medium, a thumb drive, a memory card, a RAM, PROM, and EPROM, a FLASH-EPROM, any other memory chip or cartridge, or any other tangible medium from which a computer can read.

Various forms of computer readable media may be involved in carrying one or more sequences of one or more instructions to processor 104 for execution. For example, the instructions may initially be carried on the magnetic disk of a remote computer. The remote computer can load the instructions into its dynamic memory and send the instructions over a telephone line using a modem. A modem local to computer system 100 can receive the data on the telephone line and use an infra-red transmitter to convert the data to an infra-red signal. An infra-red detector coupled to bus 102 can receive the data carried in the infra-red signal and place the data on bus 102. Bus 102 carries the data to memory 106, from which processor 104 retrieves and executes the instructions. The instructions received by memory 106 may optionally be stored on storage device 110 either before or after execution by processor 104.

In accordance with various embodiments, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

The following descriptions of various implementations of the present teachings have been presented for purposes of illustration and description. It is not exhaustive and does not limit the present teachings to the precise form disclosed. Modifications and variations are possible in light of the above teachings or may be acquired from practicing of the present teachings. Additionally, the described implementation includes software but the present teachings may be implemented as a combination of hardware and software or in hardware alone. The present teachings may be implemented with both object-oriented and non-object-oriented programming systems.

Systems and Methods of Species Detection

As noted above, the Food Standards Agency (FSA) announced recently that deoxyribonucleic acid (DNA) molecules of horse and/or pig had been identified in beef products sold by several supermarket chains, and further testing across Europe and beyond has revealed widespread incidences of such contamination. However, most testing methods either do not detect or identify proteins, or detect only one part of the protein and not multiple protein markers.

In various embodiments, methods and systems for species detection using mass spectrometry provide a rapid, robust, sensitive and specific method for the simultaneous detection of the DNA molecules in a series of meat species, for example, as well as small molecules, such as veterinary drug residues, in a single analysis. The meat species can be, for example, horse meat existing at low percentage levels in beef. Veterinary drug residues are described herein for illustration purposes, and small molecules are not limited to veterinary drug residues. One skilled in the art will appreciate that embodiments of the methods and systems can be applied to detect any other types of small molecules at the same time as detecting DNA molecules in meat species. An example of the veterinary drug residue is the banned substance phenylbutazone (BUTE).

In various embodiments, liquid chromatography-mass spectrometry/mass spectrometry (LC-MS/MS) is used to provide the simultaneous detection. LC-MS/MS is described herein for illustration purposes, and mass spectrometry is not limited to LC-MS/MS. One skilled in the art will appreciate that other types of mass spectrometry can equally be applied.

In various embodiments, methods and systems do not use polymerase chain reaction (PCR) amplification and offer a more accurate and reliable approach to meat speciation than PCR or enzyme-linked immunosorbent assay (ELISA) based techniques or other indirect methods. Further, various embodiments of the methods and systems allow for the detection of small molecules, such as veterinary drug residues, in the same analysis, which is not possible by ELISA or PCR.

In various embodiments, methods and systems use an Eksigent Ekspert™ microLC 200 ultra-high-performance LC (UHPLC) system coupled with an AB SCIEX QTRAP® 5500 LC/MS/MS system, for example. Eksigent Ekspert™ microLC 200 UHPLC system and QTRAP® 5500 LC/MS/MS system are described for illustration purposes. One skilled in the art will appreciate that any high performance separation device can be used, which includes, but is not limited to, liquid chromatography device, capillary electrophoresis device, or ion mobility device.

In various embodiments, methods and systems use multiple reaction monitoring (MRM) for the detection of peptides markers for DNA molecules in a series of meat species, such as horse meat proteins existing at low percentage in beef.

In various embodiments, methods and systems provide sequence information by acquiring an enhanced product ion (EPI) scan for each trigging MRM, which can be used to further confirm the peptide's proteins and therefore the species' identity. This provides greater confidence for food testing when distinguishing between species because, for example, horse and beef proteins may differ by as little as one or two amino acids.

In various embodiments, at the same time as detecting peptide markers for DNA molecules in a series of meat species, methods and systems can detect and quantify small molecules, such as veterinary drug residues, using the same extraction method and LC conditions as those used for detecting and quantifying the DNA molecules in a series of meat species. Specifically, additional and specific MRM transitions for small molecules are added to the same extraction method used for meat species detection. In various embodiments, non-steroidal anti-inflammatory drug (NSAID) BUTE can be detected in meat samples, for example.

Species Detection System

Figure 2:
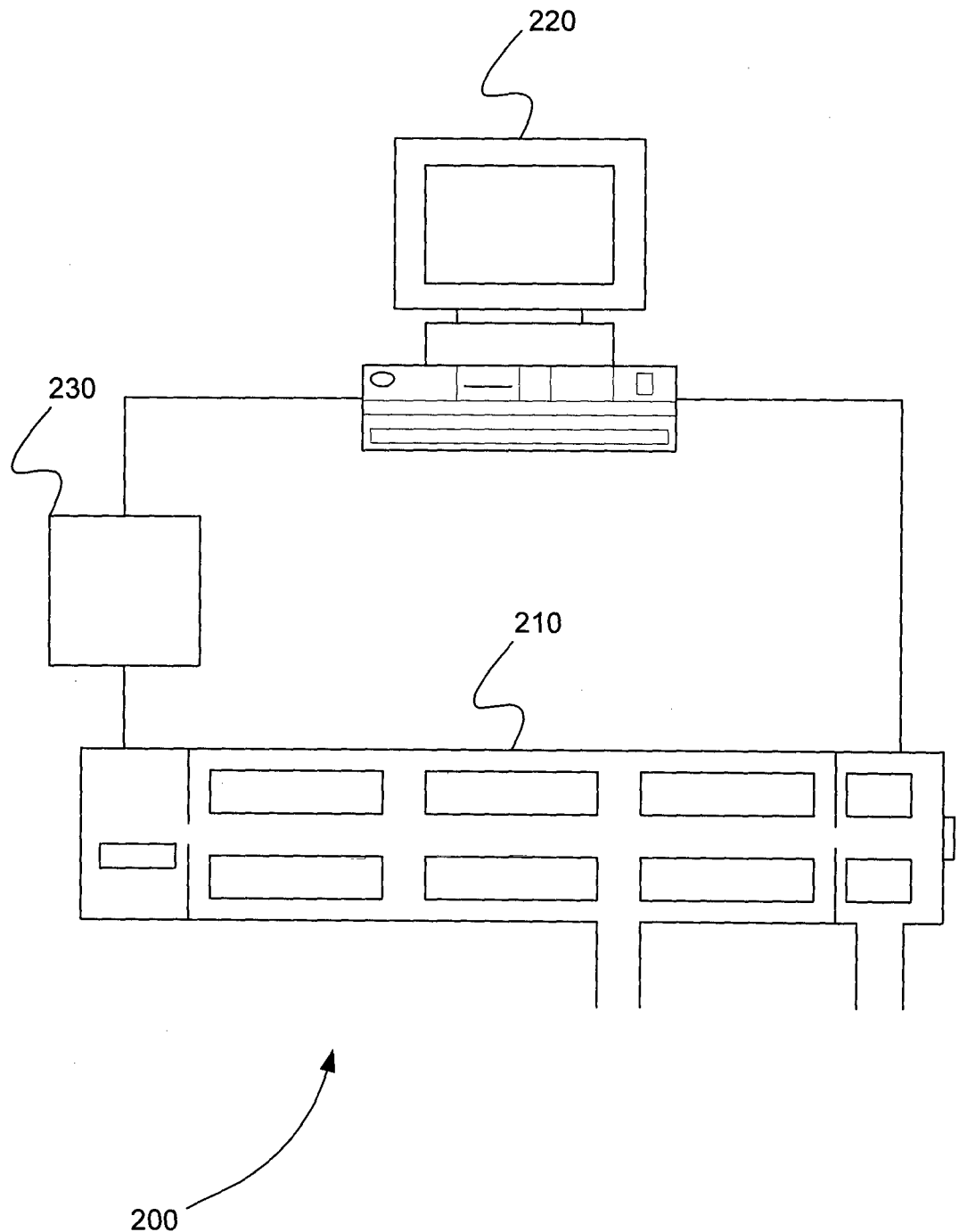
FIG. 2 is a schematic diagram showing a system for species detection using mass spectrometry, in accordance with various embodiments.

FIG. 2 is a schematic diagram showing a system 200 for species detection using mass spectrometry, in accordance with various embodiments. System 200 includes tandem mass spectrometer 210, processor 220, and separation device 230. Mass spectrometer 210 performs an MRM experiment on a sample targeting one or more peptide transitions that are unique to one or more species. Processor 220 can be, but is not limited to, a computer, microprocessor, or any device capable of sending and receiving control signals and data from mass spectrometer 210 and processing data. In various embodiments, processor 220 is in communication with tandem mass spectrometer 210 and receives one or more measured product ion spectra from tandem mass spectrometer 210.

In various embodiments, processor 220 compares the one or more measured product ion spectra to product ions of the one or more peptide transitions that are unique to one or more species.

In various embodiments, processor 220 detects one or more species of the sample by reporting product ions of the one or more peptide transitions that are unique to one or more species that match the one or more measured product ion spectra.

In various embodiments, separation device 230 can be added to system 200 to separate the sample from a mixture. Separation device 230 can perform a separation technique that includes, but is not limited to, solid phase extraction-liquid chromatography, liquid chromatography, gas chromatography, capillary electrophoresis, or ion mobility. One skilled in the art will appreciate that any other types of separation devices can be used.

In various embodiments, the sample is prepared without using a size exclusion technique. For example, the sample can be prepared using solid-phase extraction (SPE).

In various embodiments, the sample can be meat or processed meat. If processed meat is used, in various embodiments, the one or more peptide transitions that are unique to one or more species include peptides that are known not to be susceptible to a modification during food processing. In various embodiments, the modification during food processing comprises a post translational modification or a Maillard reaction.

In various embodiments, the species detection is performed without DNA amplification, or PCR.

In various embodiments, the species detection is performed without ELISA.

In various embodiments, tandem mass spectrometer 210 performs an EPI scan during the MRM experiment.

In various embodiments, tandem mass spectrometer 210 further targets one or more transitions of one or more known small molecules in the same MRM experiment. Processor 220 further compares the one or more measured product ion spectra to small molecule product ions of the one or more transitions of one or more known small molecules. Processor 220 detects one or more known small molecules of the sample along with the one or more species of the sample by reporting small molecule product ions of the one or more transitions of one or more known small molecules that match the one or more measured product ion spectra.

In various embodiments, the one or more known small molecules include residues or metabolites of veterinary drugs, BUTE, antibiotics, growth hormones, or pesticides.

In various embodiments, a species is detected in the sample with a level of detection that is less than or equal to 1% of the sample. The level of detection is 1% when this percentage level is specifically targeted. For example, detection of 1% horse meat in beef, for example, can be achieved when 1% is specifically targeted. This 1% level of detection is described for illustration purposes, and the level of detection is not limited to 1%. One skilled in the art will appreciate that various levels of detection can equally be achieved. For example, using a higher performing platform, such as an AB SCIEX QTRAP® 6500 LC/MS/MS system, detection of lower percentage levels is possible. Also, at this 1% level, multiple markers can be detected rather than individual markers in other methods. One skilled in the art will also appreciate that detection of even lower percentage levels can be achieved using LC-MS techniques as they are further developed in the near future.

Species Detection Method

Figure 3:
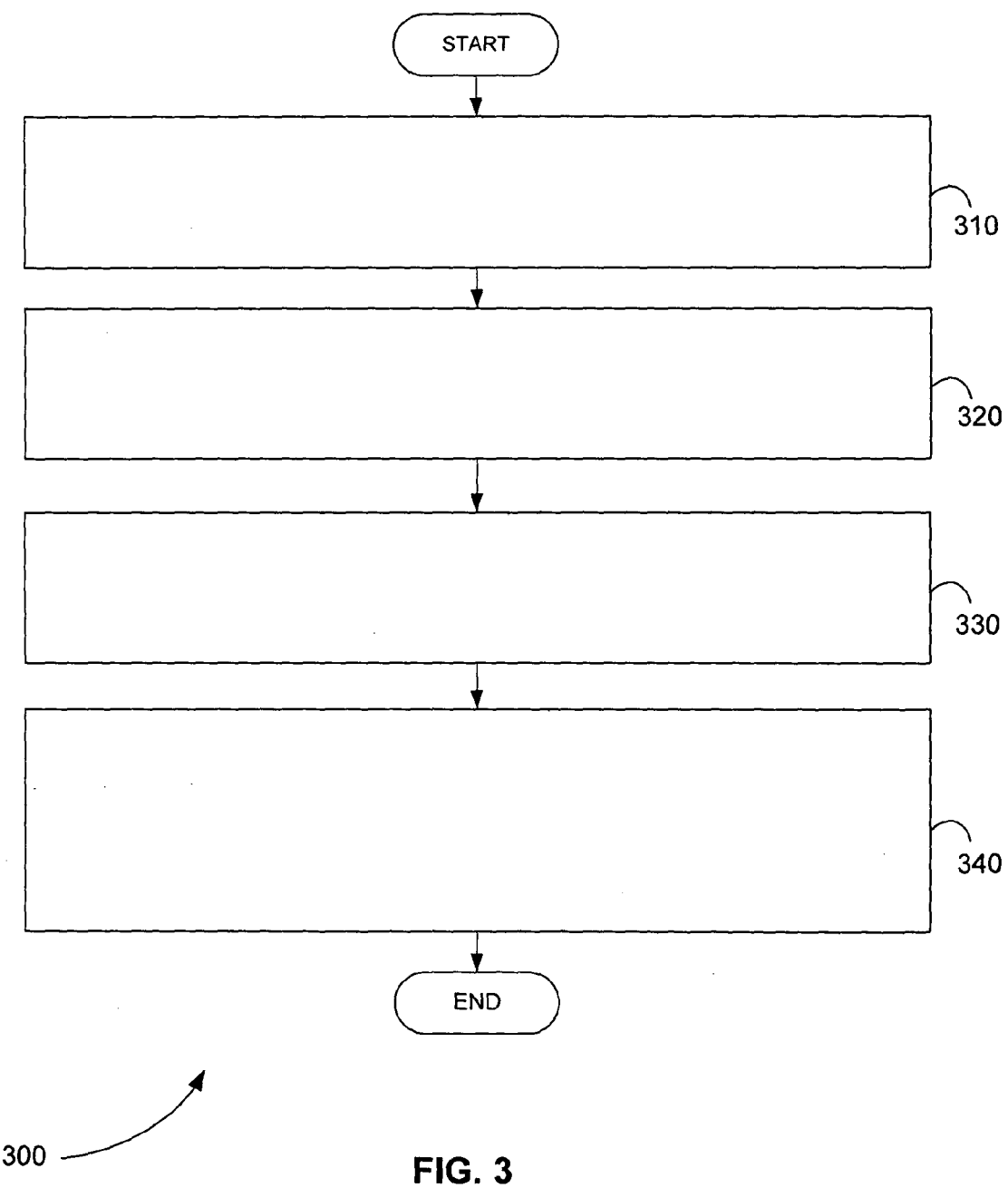
FIG. 3 is an exemplary flowchart showing a method for species detection using mass spectrometry, in accordance with various embodiments.

FIG. 3 is an exemplary flowchart showing a method 300 for species detection using mass spectrometry, in accordance with various embodiments.

In step 310 of method 300, an MRM experiment is performed on a sample targeting one or more peptide transitions that are unique to one or more species using a tandem mass spectrometer.

In step 320, one or more measured product ion spectra are received from the tandem mass spectrometer using the processor.

In step 330, the one or more measured product ion spectra are compared to product ions of the one or more peptide transitions that are unique to one or more species using the processor.

In step 340, one or more species of the sample are detected by reporting product ions of the one or more peptide transitions that are unique to one or more species that match the one or more measured product ion spectra using the processor.

Species Detection Computer Program Product

In various embodiments, a computer program product includes a tangible computer-readable storage medium whose contents include a program with instructions being executed on a processor so as to perform a method for species detection using mass spectrometry. This method is performed by a system that includes one or more distinct software modules.

Figure 4:
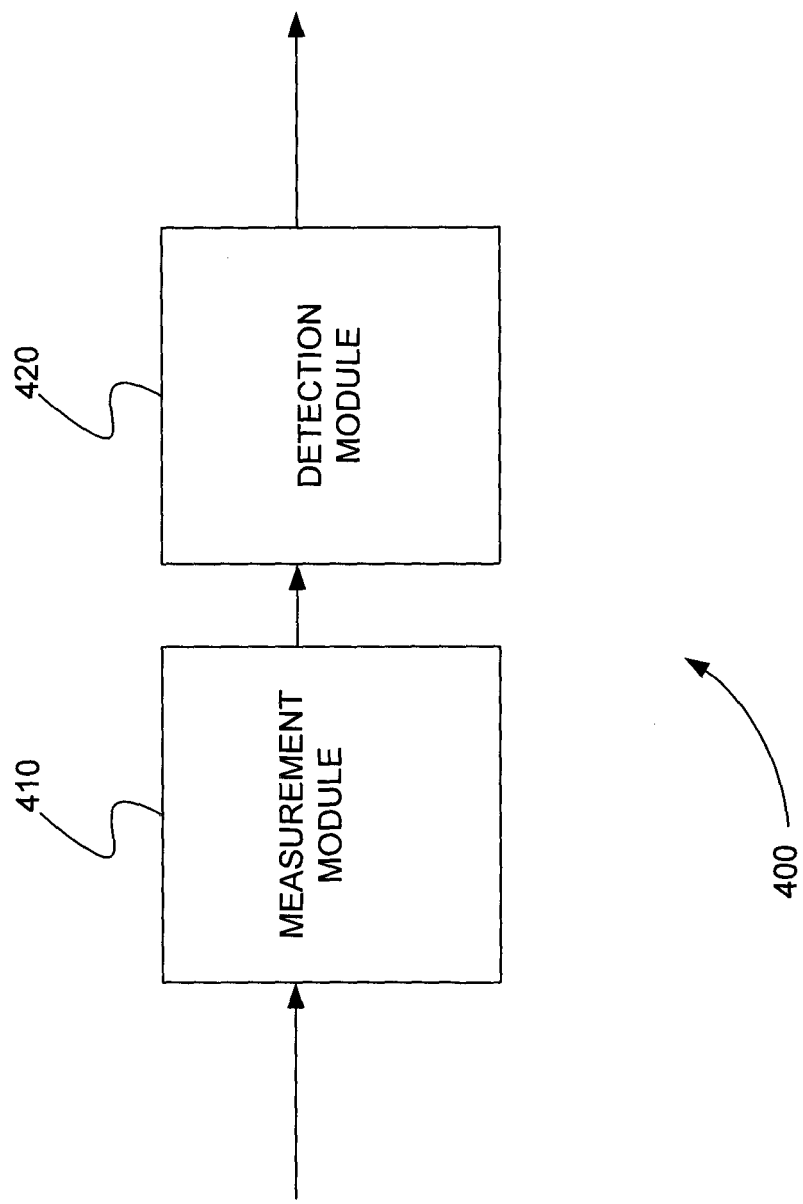
FIG. 4 is a schematic diagram of a system that includes one or more distinct software modules that performs a method for species detection using mass spectrometry, in accordance with various embodiments.

FIG. 4 is a schematic diagram of a system 400 that includes one or more distinct software modules that performs a method for species detection using mass spectrometry, in accordance with various embodiments. System 400 includes measurement module 410 and detection module 420.

Measurement module 410 receives one or more measured product ion spectra from the tandem mass spectrometer that performs a multiple reaction monitoring (MRM) experiment on a sample targeting one or more peptide transitions that are unique to one or more species.

Detection module 420 compares the one or more measured product ion spectra to product ions of the one or more peptide transitions that are unique to one or more species.

Detection module 420 detects one or more species of the sample by reporting product ions of the one or more peptide transitions that are unique to one or more species that match the one or more measured product ion spectra.

Data Examples

In an exemplary experiment, some commercially available target proteins were used, as well as some commercially available reference materials of pork, beef, and horse meat. Also, beef reference materials that had been spiked at different levels with horse meat were used. A sample of lamb meat was used.

In this experiment, a sigma standard of BUTE was not available. Therefore, BUTE was extracted from a sample of horse medicine.

Sample Preparation

The meat sample was homogenized using a food processor and mixed (2 g) with an extraction buffer containing tris(2-amino-2-hydroxymethyl-propane-1,3-diol), urea and acetonitrile (10 mL). The meat was broken up by shaking, ultra sonication (15 min) and agitated further using a roller mixer (45 min). This mixture was centrifuged and the top liquid layer (0.5 mL) was transferred to a 2 mL Eppendorf tube. The protein markers were reduced in a thermal mixer with a solution of tris(2-carboxyethyl)phosphine (TCEP, 60 min, 60° C.), alkylated by adding methyl methanethiosulfonate (MMTS, 30 min, room temperature in the dark) and digested in a thermal mixer by addition of a digestion buffer containing ammonium bicarbonate, calcium chloride and trypsin (60 min, 40° C.).

The filtrate was purified using a conventional conditioned polymeric solid-phase extraction (SPE) cartridge from Phenomenex. The peptides were extracted from the cartridge using acetonitrile and the extract was evaporated to dryness and reconstituted in acidified aqueous acetonitrile.

LC Separation

All method development and analysis were done using an Eksigent Ekspert™ microLC 200 UHPLC system. Final extracted samples (10 μL) were separated over an 11 minute gradient (Table 1) where A=water and B=acetonitrile both containing 0.1% formic acid. Peptides were separated on a reversed-phase Halo C18 2.7 μm 90 Å 50×0.5 mm (Eksigent) column at 20 μL/min and at a temperature of 40° C.

Figure 5:
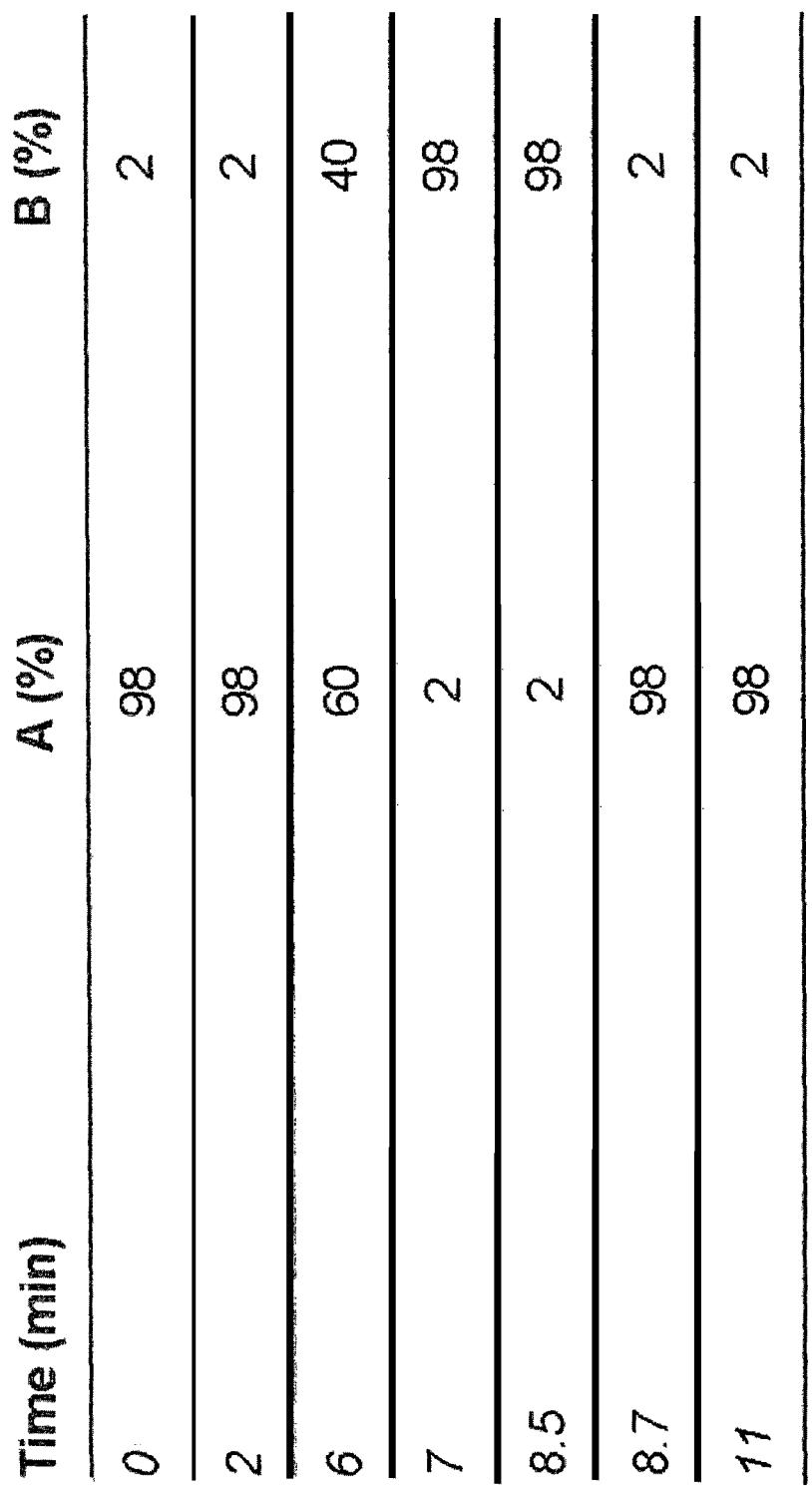
FIG. 5 is an exemplary table illustrating the gradient conditions used for separation in an exemplary species detection experiment, in accordance with various embodiments.

FIG. 5 is an exemplary table 500 illustrating the gradient conditions used for separation, in accordance with various embodiments.

MS/MS Detection

In this experiment, all analyses were performed on an AB SCIEX QTRAP® 5500 LC/MS/MS system.

LC/MS/MS System Using Electrospray Ionization (ESI).

Figure 6:
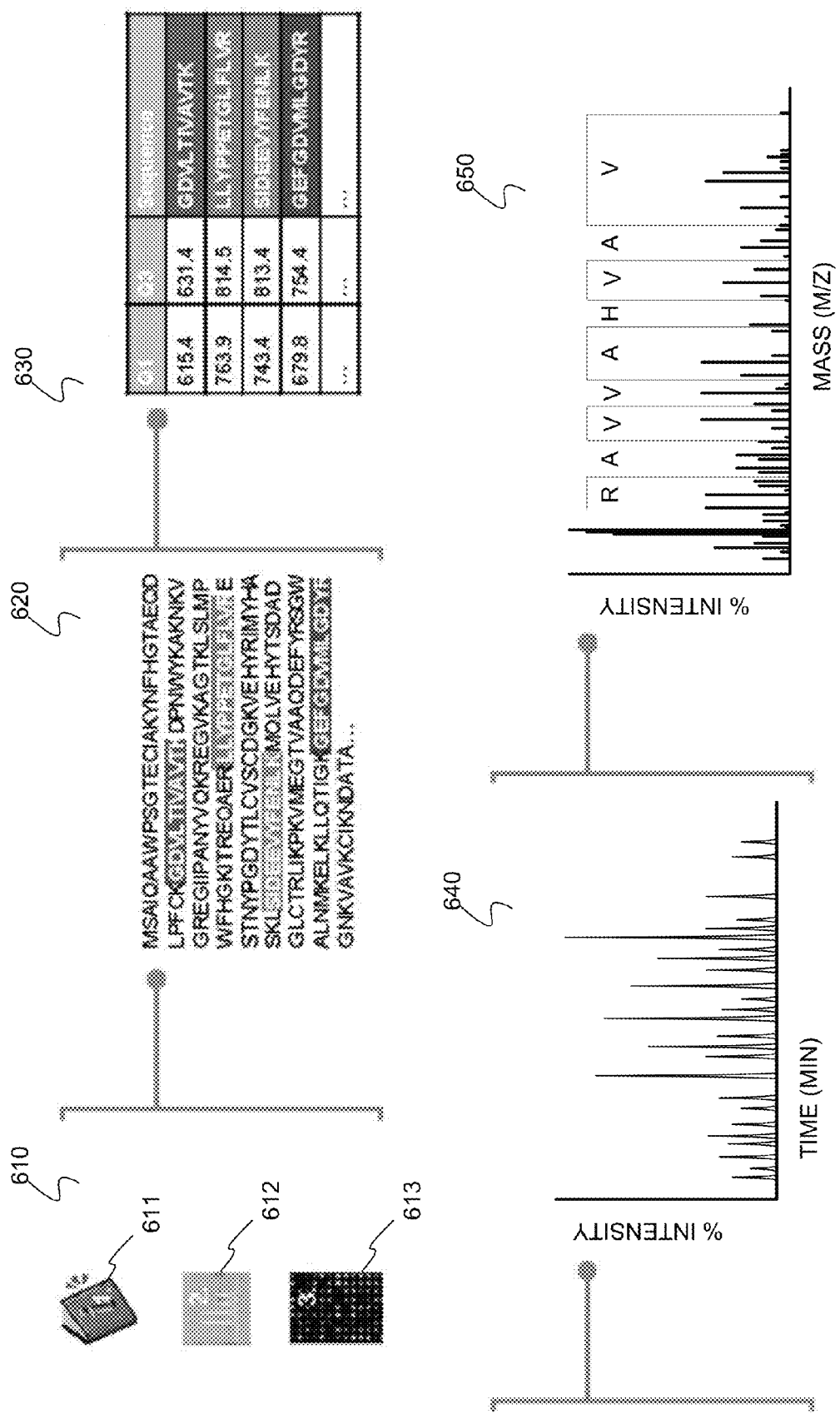
FIG. 6 is an exemplary MRM-initiated detection and sequencing (MIDAS™) workflow for an exemplary species detection experiment, in accordance with various embodiments.

FIG. 6 is an exemplary MRM-initiated detection and sequencing (MIDAS™) workflow 600, in accordance with various embodiments. Workflow 600 includes step 610 through 650. In step 610, information from the literature 611, proteomics 612, and genomics 613 is gathered. In step 620, a protein sequence is found. In step 630, in silico (or simulated on a computer) MRM transitions are found. In step 640, MRM detection in a biological mixture is performed using the MRM transitions found. Finally, in step 650, tandem mass spectrometry is used for identification in samples.

In this experiment, an MIDAS™ workflow was used where the electrode was changed to a microLC hybrid electrode (50 μm ID) designed for MicroLC. For MIDAS™, a set of predicted MRM transitions from the known protein sequence were used as a survey scan to trigger the acquisition of EPI spectra (shown in FIG. 7).

Figure 7:
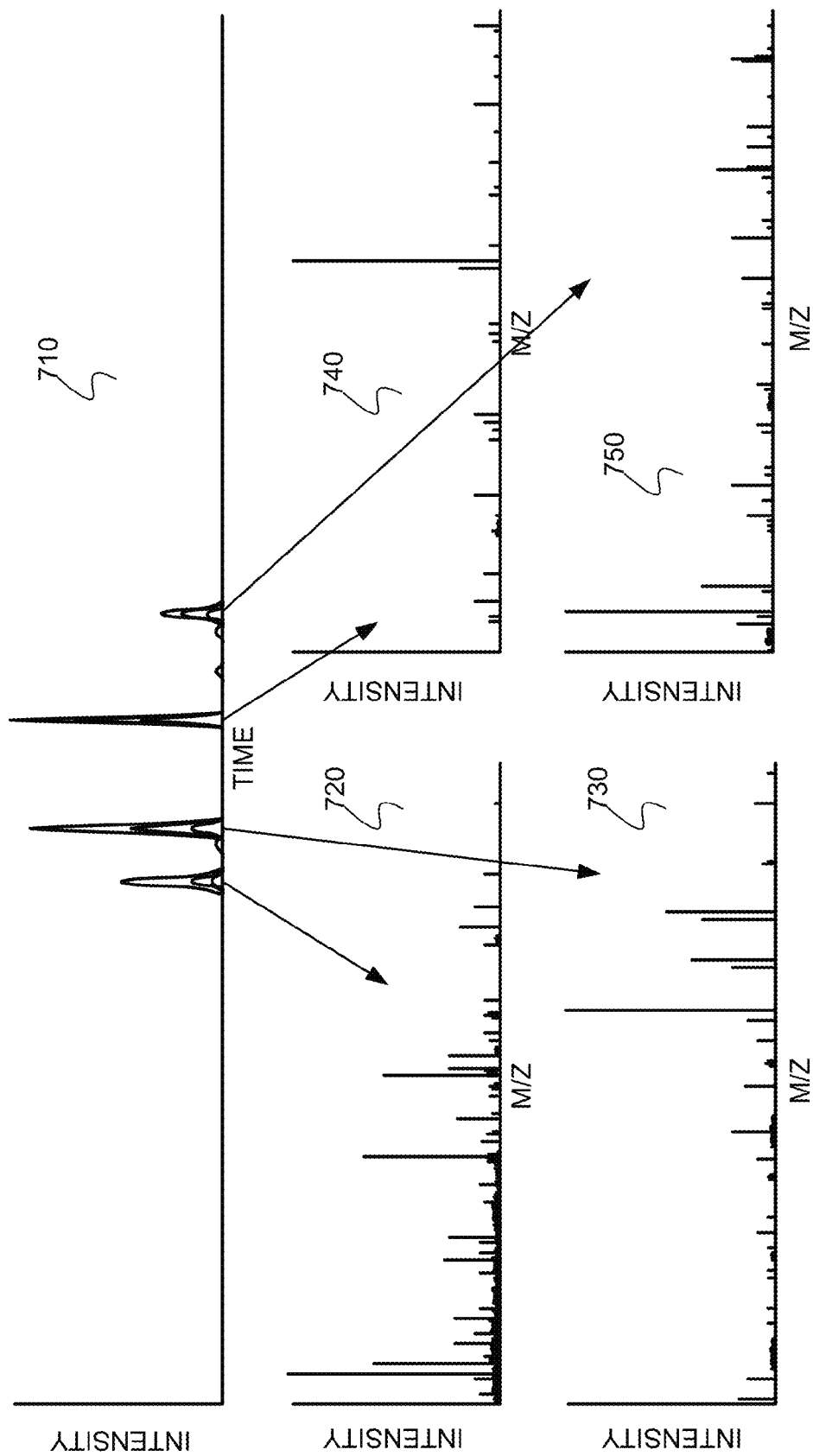
FIG. 7 is an exemplary series of plots showing MRM initiated acquisition of mass spectrometry/mass spectrometry (MS/MS) spectra to sequence characteristic proteins for horse meat, in accordance of various embodiments.

FIG. 7 is an exemplary series of plots 700 showing MRM initiated acquisition of MS/MS spectra to sequence characteristic proteins for horse meat, in accordance of various embodiments. Plot 710 is a plot of four extracted-ion chromatograms (XICs or EICs) for four MRM transitions. Plots 720-750 are the product ion (MS/MS) spectra showing the sequence for each XIC.

This data was then submitted to a database search engine for confirmation of peptide identification and of the feasibility of the MRM transition for meat speciation. With this workflow MRM transitions were designed without the need for synthetic peptides.

Figure 8:
FIG. 8 is an exemplary table illustrating MRM transitions for the detection of phenylbutazone (BUTE) for an exemplary species detection experiment, taken from the iMethod™ application for Antibiotic Screening Version 1.3, in accordance with various embodiments.

FIG. 8 is an exemplary table 800 illustrating MRM transitions for the detection of BUTE, taken from the iMethod™ application for Antibiotic Screening Version 1.3, in accordance with various embodiments. In the last step of this experiment, the TurboV™ source conditions used were gas 1, gas 2 and the curtain gas was set to 30 psi, the temperature of the source was set at 350° C. and the IS voltage was 5500 V. The peptides and BUTE were analyzed using the Scheduled MRM™ algorithm with an MRM detection window of 50 s and a target scan time of 0.40 s. Q1 resolution was set to low and Q3 resolution was set to unit. A total of 56 MRM transitions were used over the 11 minute run time with 3 dedicated to BUTE, 12 for horse meat (4 peptides with 3 MRM transitions each) and the rest for other meat species peptides currently under evaluation.

In the experiment, the MRM conditions for the detection of BUTE were taken from the MRM catalogue of the iMethod™ application for Veterinary Antibiotic Screening 1.1, for example (as shown in FIG. 8).

Results and Discussion of the Experiment

In the experiment, care was taken to make sure that peptides chosen were unique to the meat species. The list was further consolidated by removing peptides that could be susceptible to modification during food processing, e.g., undergo post translational modification or the Maillard reaction (for future application to processed meat samples). This reduced the number of peptides used as triggers for detection and generation of peptide finger prints of species.

Figure 9:
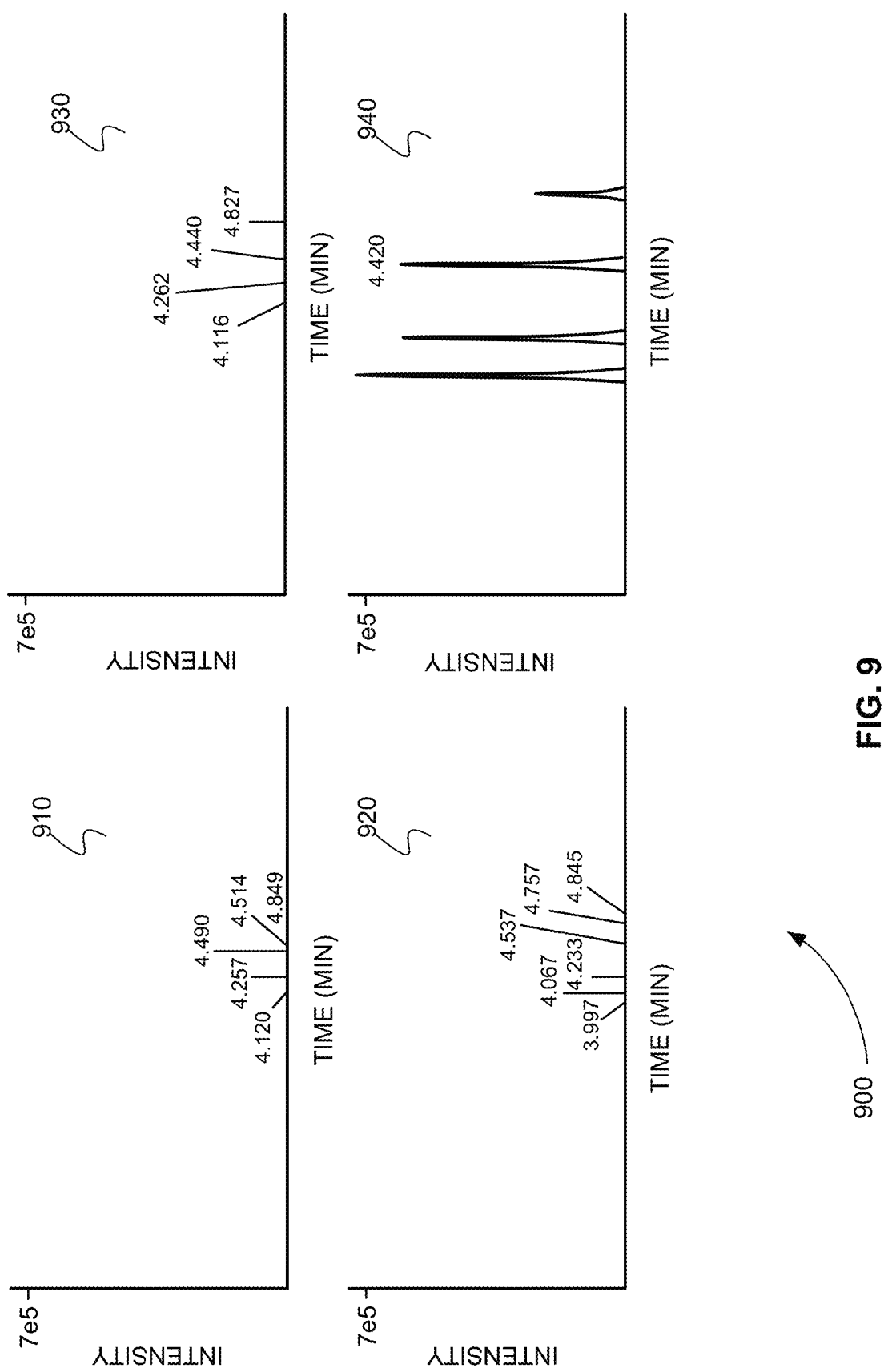
FIG. 9 is an exemplary series of plots showing a comparison of the analysis of extracts from different types of meat, including horse, beef, pork and lamb extracts, in accordance with various embodiments.

FIG. 9 is an exemplary series of plots 900 showing a comparison of the analysis of extracts from different types of meat, including horse, beef, pork and lamb extracts, in accordance with various embodiments. Plots 910-940 are XIC plots for lamb, beef, pork, and horse, respectively. In plot 940, unique peptides for horse are shown from a method which contains additional markers for other species that are currently under evaluation. This confirmed that the BLAST search results for the specific peptides chosen for horse meat were specific to horse and were not seen in beef, pork and lamb.

Figure 10:
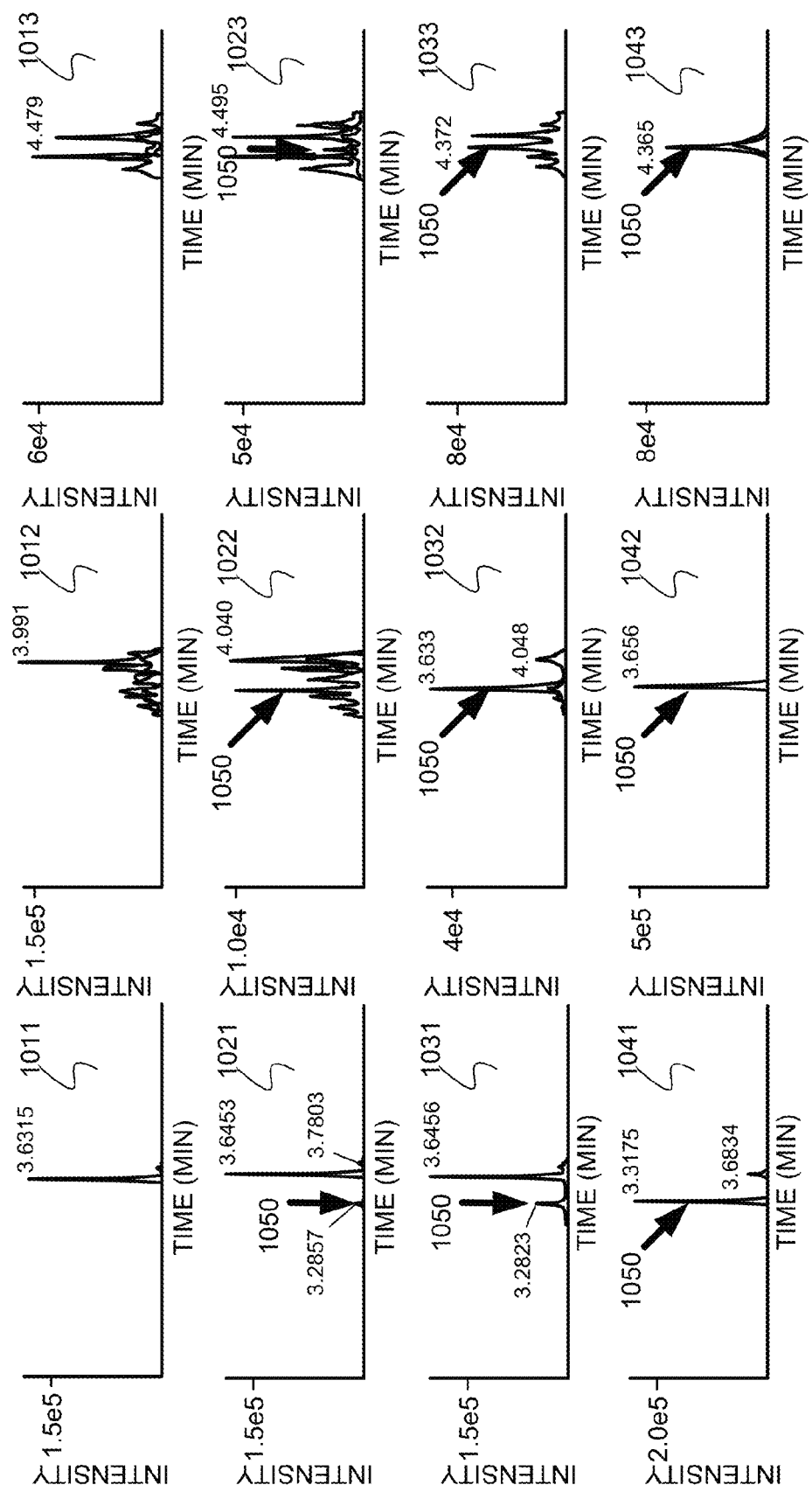
FIG. 10 is an exemplary series of plots showing the comparison of beef and beef reference material that had been spiked at 10% and at 1% horse (current detection limit for polymerase chain reaction (PCR) analysis) for an exemplary species detection experiment, in accordance with various embodiments.

FIG. 10 is an exemplary series of plots 1000 showing the comparison of beef and beef reference material that had been spiked at 10% and at 1% horse (current detection limit for PCR analysis), in accordance with various embodiments. In this figure the MRM transitions for 3 of the 4 peptides have been extracted and it shows that horse meat can be detected at a 1% spike level. The fourth peptide was detected at 10% level and it was below the LOD limit at 1% horse meat in beef. Plots 1011-1013 are XIC plots for beef alone. Plots 1021-1023 are XIC plots for 1% horse in beef. Plots 1031-1033 are XIC plots for 10% horse in beef. Plots 1041-1043 are XIC plots for horse alone. Arrows 1050 indicate horse meat.

In order to confirm these results, extraction of samples were performed multiple times and in each batch 1% horse meat could be detected in beef.

Figure 11:
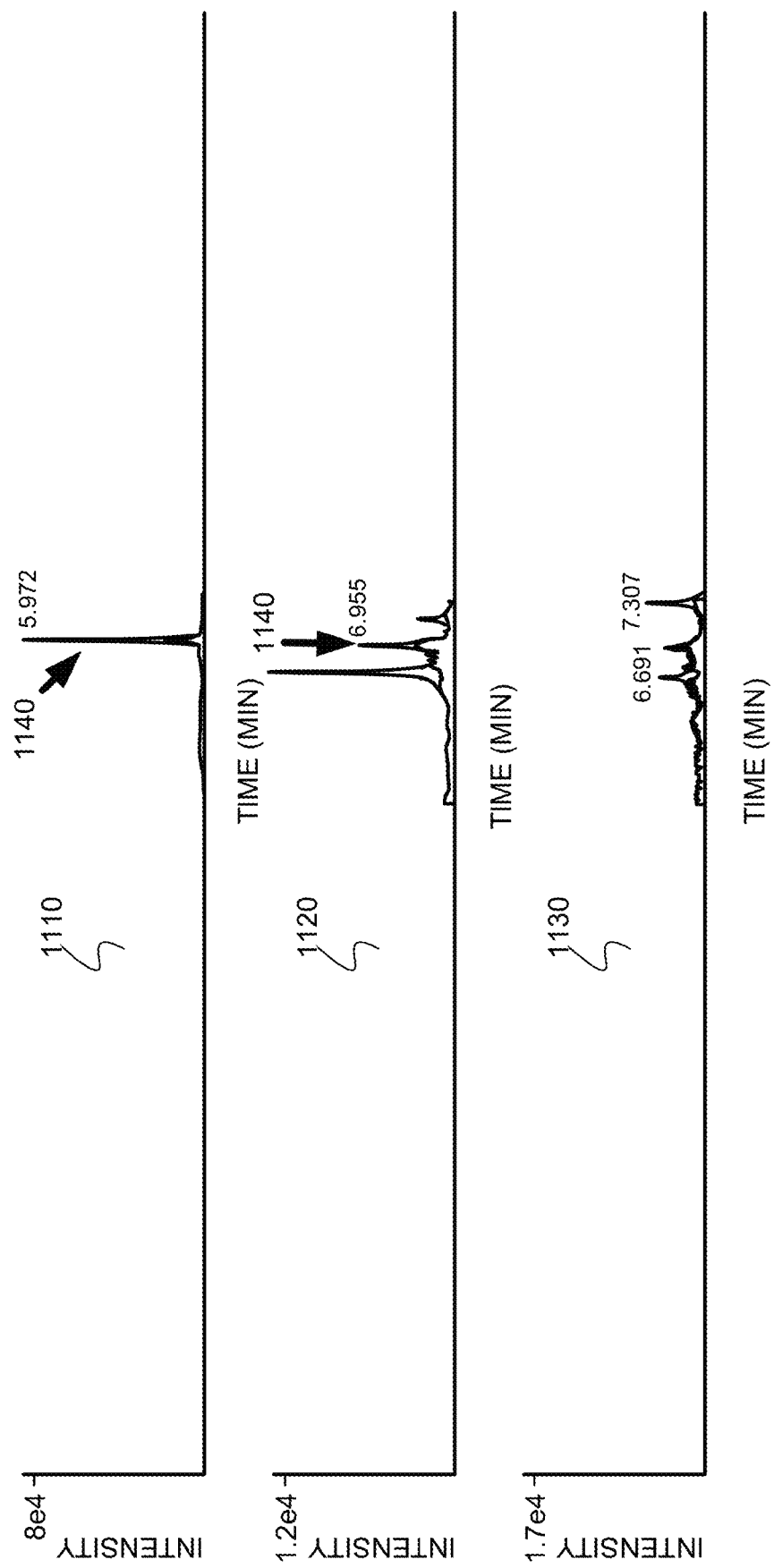
FIG. 11 is an exemplary series of plots showing extracted ion chromatograms for BUTE in a blank and a spiked sample of meat at a level below 10 µg/kg, in accordance with various embodiments.

FIG. 11 is an exemplary series of plots 1100 showing extracted ion chromatograms for BUTE in a blank and a spiked sample of meat at a level below 10 µg/kg that had been extracted using the same protocol, in accordance with various embodiments. Plot 1110 is an XIC for a BUTE standard. Plot 1120 is an XIC for a horse meat extract spiked at 2.5 µg/kg. Plot 1130 is an XIC for a horse meat extract. Arrows 1140 indicate horse BUTE. At the time of these initial tests the pure standard was not available so BUTE had been extracted from commercially available horse medicine.

Levels in the extract were assumed to be lower than 10 µg/kg and this work is planned to be repeated using spiking experiments with analytical standard grade phenylbutazone. Also as this particular horse meat sample was just for speciation testing the work will be repeated using beef that should be totally clear of BUTE.

Summary of the Experiment

LC-MS/MS offered a rapid, robust, sensitive and specific assay for the simultaneous detection of the DNA in a series of meat species, for example, as well as small molecules, such as veterinary drug residues, in a single analysis.

Sensitivities achieved were equivalent to sensitivities of some currently available methods based on ELISA and real-time PCR.

The LC-MS/MS approach has the additional advantage of being a potential multi species screen unlike ELISA where individual meat species are detected by separate kits. By using the MIDAS™ workflow full scan QTRAP® MS/MS spectra can also be obtained at the same time as quantitative information, confirming multiple peptide target identification and reducing the occurrence of false positives associated with other techniques.

Although the above experiment shows that the detection is qualitative, quantitation can be achieved when internal standards is used. Unlike PCR or ELISA, LC-MS/MS has the ability to detect small molecules, such as banned veterinary drug residues, as well as meat speciation in the same analysis.

Meat authenticity is described above for illustration purposes. One skilled in the art will appreciate that other types of authenticity can equally be applied, which include, but are not limited to fish authenticity, plant authenticity, and honey authenticity. Fish authenticity involves, for example, simultaneous detection of various fish species and chemical residues, such as small molecules including veterinary drug residues and antibiotics. Plant authenticity involves, for example, simultaneous detection of various plant species and chemical residues, such as small molecules including veterinary drug residues and antibiotics. Honey authenticity involves, for example, simultaneous detection of various honey species and chemical residues, such as small molecules including veterinary drug residues and antibiotics.

Additional Species Detection Methods

Figure 12:
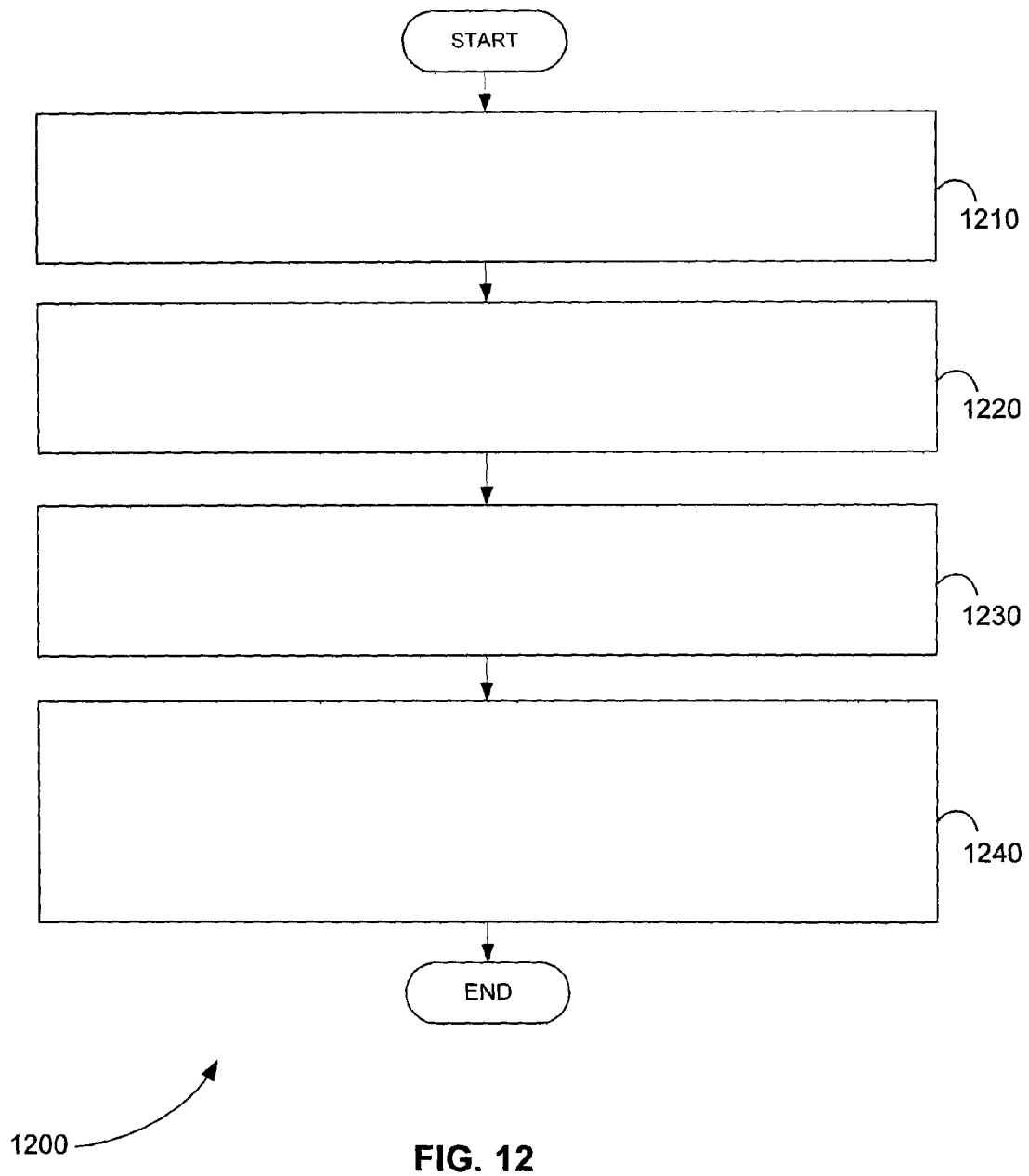
FIG. 12 is an exemplary flowchart showing a method for species detection based on one or more peptide transitions and one or more small molecule transitions using tandem mass spectrometry, in accordance with various embodiments.

FIG. 12 is an exemplary flowchart showing a method 1200 for species detection based on one or more peptide transitions and one or more small molecule transitions using tandem mass spectrometry, in accordance with various embodiments.

In step 1210 of method 1200, a multiple reaction monitoring (MRM) experiment is performed on a sample targeting one or more peptide transitions that are unique to one or more species and one or more transitions of one or more known small molecules using a tandem mass spectrometer. The sample is prepared without using a size exclusion technique and without using deoxyribonucleic acid (DNA) amplification.

In step 1220, one or more measured product ion spectra are received from the tandem mass spectrometer using the processor.

In step 1230, the one or more measured product ion spectra are compared to product ions of the one or more peptide transitions that are unique to one or more species and to small molecule product ions of the one or more transitions of one or more known small molecules using the processor.

In step 1240, one or more species and one or more known small molecules of the sample are detected by reporting product ions of the one or more peptide transitions that are unique to one or more species that match the one or more measured product ion spectra and reporting small molecule product ions of the one or more transitions of one or more known small molecules that match the one or more measured product ion spectra using the processor.

Figure 13:
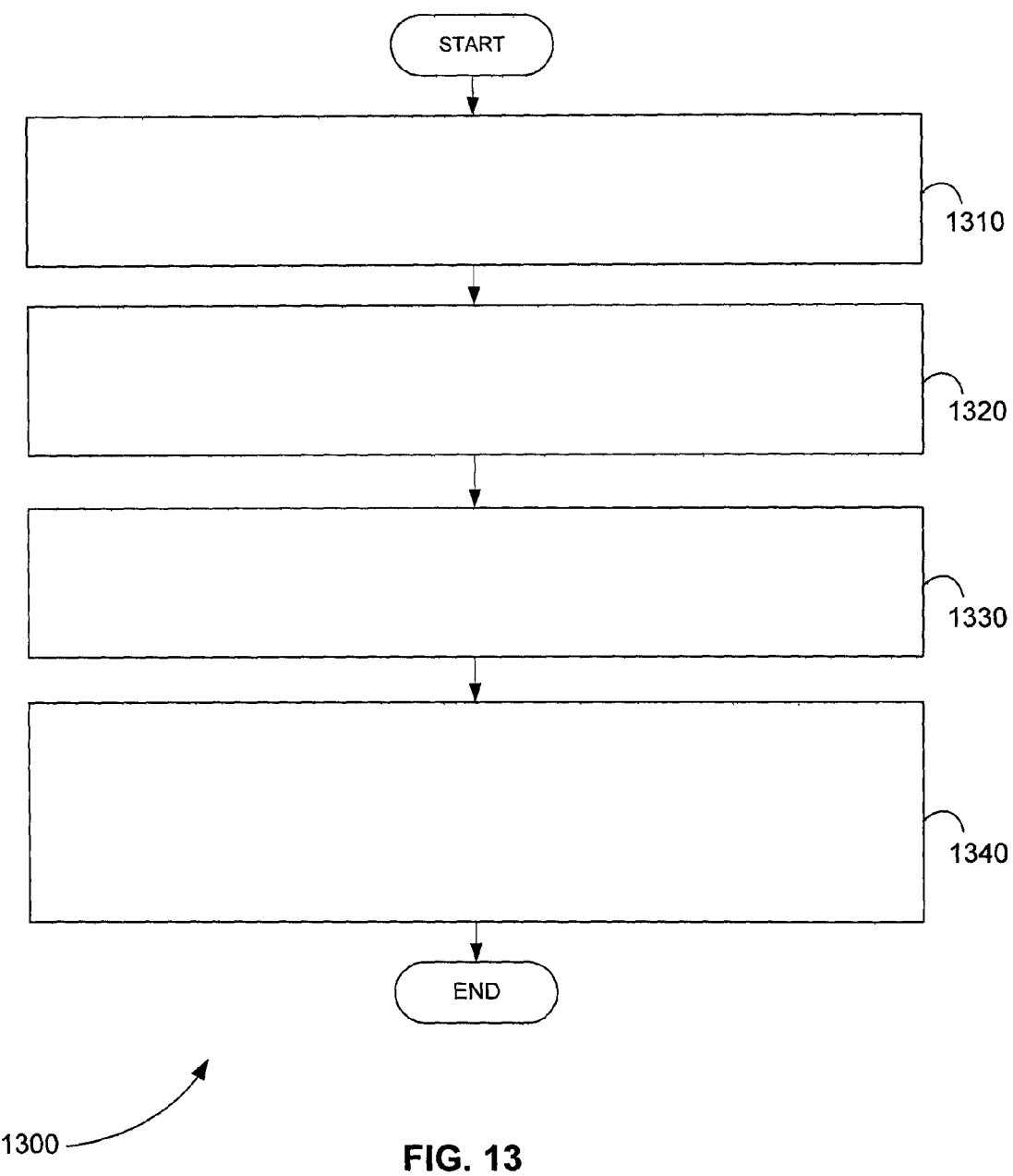
FIG. 13 is an exemplary flowchart showing a method for species detection where the sample is prepared without using a size exclusion technique and without using deoxyribonucleic acid (DNA) amplification using tandem mass spectrometry, in accordance with various embodiments.

FIG. 13 is an exemplary flowchart showing a method 1300 for species detection where the sample is prepared without using a size exclusion technique and without using deoxyribonucleic acid (DNA) amplification using tandem mass spectrometry, in accordance with various embodiments.

In step 1310 of method 1300, a multiple reaction monitoring (MRM) experiment is performed on a sample targeting one or more peptide transitions that are unique to one or more species using a tandem mass spectrometer. The sample is prepared without using a size exclusion technique and without using deoxyribonucleic acid (DNA) amplification.

In step 1320, one or more measured product ion spectra are received from the tandem mass spectrometer using the processor.

In step 1330, the one or more measured product ion spectra are compared to product ions of the one or more peptide transitions that are unique to one or more species using the processor.

In step 1340, one or more species of the sample are detected by reporting product ions of the one or more peptide transitions that are unique to one or more species that match the one or more measured product ion spectra using the processor.

In various embodiments, the sample is prepared using a solid phase extraction (SPE).

In various embodiments, sample comprises meat or processed meat.

In various embodiments, one or more transitions of one or more known small molecules are targeted in the same MRM experiment using the tandem mass spectrometer. One or more measured product ion spectra are compared to small molecule product ions of the one or more transitions of one or more known small molecules using the processor. One or more known small molecules of the sample are detected along with the one or more species of the sample by reporting small molecule product ions of the one or more transitions of one or more known small molecules that match the one or more measured product ion spectra using the processor.

In various embodiments, the one or more known small molecules comprise residues or metabolites of one or more of veterinary drugs, phenylbutazone (BUTE), antibiotics, growth hormones, and pesticides.

In various embodiments, a species is detected in the sample with a level of detection that is less than or equal to 1% of the sample.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

What is claimed is:

1. A system for species detection using tandem mass spectrometry, comprising:
    a tandem mass spectrometer that performs a multiple reaction monitoring (MRM) experiment on a sample targeting one or more peptide transitions that are unique to one or more species; and
    a processor in communication with the tandem mass spectrometer that
        receives one or more measured product ion spectra from the tandem mass spectrometer,
        compares the one or more measured product ion spectra to product ions of the one or more peptide transitions that are unique to one or more species, and
        detects one or more species of the sample by reporting product ions of the one or more peptide transitions that are unique to one or more species that match the one or more measured product ion spectra.

2. The system of claim 1, further comprising a separation device that separates the sample from a mixture.

3. The system of claim 1, wherein the sample is prepared using a solid phase extraction (SPE).

4. The system of claim 1, wherein the sample comprises meat.

5. The system of claim 1, wherein the sample comprises processed meat.

6. The system of claim 1, wherein the sample is prepared without using a size exclusion technique.

7. The system of claim 1, wherein the sample is prepared without using deoxyribonucleic acid (DNA) amplification.

8. The system of claim 1, wherein the tandem mass spectrometer performs an enhanced product ion (EPI) scan during the MRM experiment.

9. The system of claim 1, wherein
    the tandem mass spectrometer further targets one or more transitions of one or more known small molecules in the same MRM experiment,
    the processor further
        compares the one or more measured product ion spectra to small molecule product ions of the one or more transitions of one or more known small molecules, and
        detects one or more known small molecules of the sample along with the one or more species of the sample by reporting small molecule product ions of the one or more transitions of one or more known small molecules that match the one or more measured product ion spectra.

10. The system of claim 9, wherein the one or more known small molecules comprise residues or metabolites of one or more of veterinary drugs, phenylbutazone (BUTE), antibiotics, growth hormones, and pesticides.

11. A method for species detection using tandem mass spectrometry, comprising:
    performing a multiple reaction monitoring (MRM) experiment on a sample targeting one or more peptide transitions that are unique to one or more species using a tandem mass spectrometer;
    receiving one or more measured product ion spectra from the tandem mass spectrometer using a processor;
    comparing the one or more measured product ion spectra to product ions of the one or more peptide transitions that are unique to one or more species using the processor; and detecting one or more species of the sample by reporting product ions of the one or more peptide transitions that are unique to one or more species that match the one or more measured product ion spectra using the processor.

12. The method of claim 11, wherein the sample comprises meat.

13. The method of claim 11, further comprising
targeting one or more transitions of one or more known small molecules in the same MRM experiment using the tandem mass spectrometer,
comparing the one or more measured product ion spectra to small molecule product ions of the one or more transitions of one or more known small molecules using the processor, and
detecting one or more known small molecules of the sample along with the one or more species of the sample by reporting small molecule product ions of the one or more transitions of one or more known small molecules that match the one or more measured product ion spectra using the processor.

14. The method of claim 13, wherein the one or more known small molecules comprise residues or metabolites of one or more of veterinary drugs, phenylbutazone (BUTE), antibiotics, growth hormones, and pesticides.

15. The method of claim 11, wherein the sample is prepared using a solid phase extraction (SPE).

16. The method of claim 11, wherein the sample comprises processed meat.

17. The method of claim 11, wherein the sample is prepared without using a size exclusion technique.

18. The method of claim 11, wherein the sample is prepared without using deoxyribonucleic acid (DNA) amplification.

19. The method of claim 11, wherein the tandem mass spectrometer performs an enhanced product ion (EPI) scan during the MRM experiment.

20. A computer program product, comprising a tangible computer-readable storage medium whose contents include a program with instructions being executed on a processor so as to perform a method for species detection using mass spectrometry, the method comprising:
providing a system, wherein the system comprises one or more distinct software modules, and wherein the distinct software modules comprise a measurement module and a detection module;
receiving one or more measured product ion spectra from a tandem mass spectrometer that performs a multiple reaction monitoring (MRM) experiment on a sample targeting one or more peptide transitions that are unique to one or more species using the measurement module;
comparing the one or more measured product ion spectra to product ions of the one or more peptide transitions that are unique to one or more species using the detection module; and
detecting one or more species of the sample by reporting product ions of the one or more peptide transitions that are unique to one or more species that match the one or more measured product ion spectra using the detection module.

* * * * *